United States Patent
Arnold

(12) 
(10) Patent No.: US 6,177,576 B1
(45) Date of Patent: Jan. 23, 2001

(54) PYRUVATE SACCHARIDE KETALS

(76) Inventor: Michael J. Arnold, 4521 Campus Dr., #225, Irvine, CA (US) 92715

( * ) Notice: Under 35 U.S.C. 154(b), the term of this patent shall be extended for 0 days.

(21) Appl. No.: 09/129,528

(22) Filed: Aug. 5, 1998

Related U.S. Application Data

(60) Provisional application No. 60/054,766, filed on Aug. 5, 1997.

(51) Int. Cl.$^7$ .......... A61K 31/36; A61K 31/357; C07D 317/26; C07D 319/06
(52) U.S. Cl. .......... 549/372; 514/467; 514/452; 549/373; 549/450; 549/452
(58) Field of Search .................. 549/372, 373, 549/450, 452; 514/452, 467

(56) References Cited

U.S. PATENT DOCUMENTS

| | | |
|---|---|---|
| 4,158,057 | 6/1979 | Stanko . |
| 4,351,835 | 9/1982 | Stanko . |
| 4,415,576 | 11/1983 | Stanko . |
| 4,548,937 | 10/1985 | Stanko . |
| 4,645,764 | 2/1987 | Stanko . |
| 4,812,479 | 3/1989 | Stanko . |
| 4,874,790 | 10/1989 | Stanko . |
| 5,134,162 | 7/1992 | Stanko . |
| 5,294,641 | 3/1994 | Stanko . |
| 5,480,909 | 1/1996 | Stanko . |
| 5,508,308 | 4/1996 | Miller et al. . |
| 5,744,498 | 4/1998 | Stanko . |

OTHER PUBLICATIONS

Newman et al., J. Org. Chem., vol. 38 (6), 1973, 1173–77.*

* cited by examiner

Primary Examiner—Joseph K. McKane
Assistant Examiner—Taofiq A. Solola
(74) Attorney, Agent, or Firm—Lyon & Lyon LLP

(57) ABSTRACT

A novel composition for supplementing the human diet having a polyol-derived pyruvate (2-keto-propionic-acid) moeity as a component.

1 Claim, 1 Drawing Sheet and

X = ester (OR)
  = amide (NR$_2$)
  = acid (OH)
  = acidsalt (OM)

R = alkyl, polyol, H

M = Na, K, Mg, Ca

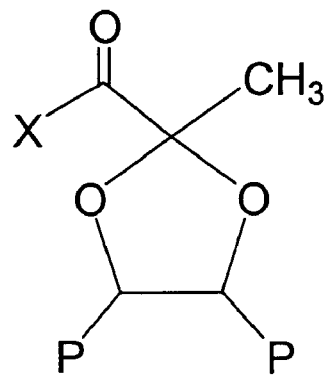 and 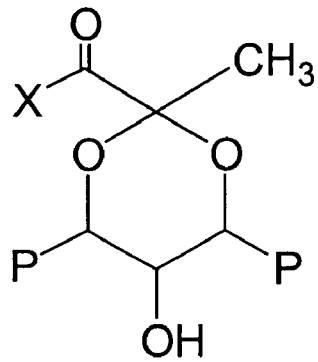
X = ester (OR)  R = alkyl, polyol, H
 = amide ($NR_2$)
 = acid (OH)
 = acidsalt (OM)  M = Na, K, Mg, Ca
P = H,
 = polyol
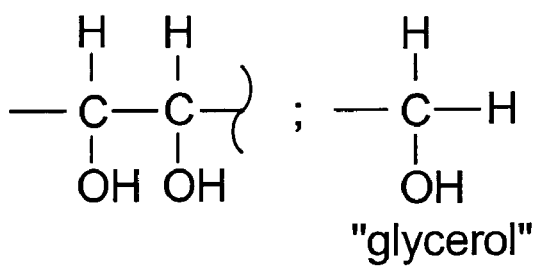
"glycerol"

PYRUVATE SACCARIDE KETALS

This appln claims the benefit of Provisional Application No. 60/054,766 filed Aug. 5, 1997.

FIELD OF THE INVENTION

The present invention relates to the field of dietary compositions useful for supplementation of the human diet, and to methods for producing said compositions.

BACKGROUND OF THE INVENTION

Pyruvic acid and its salts (as well as esters and amides) have been described as beneficial for use to supplement the human diet. Such benefits include protection from harmful oxidation (anti-oxidant), energy enhancement and endurance, fat reduction and the promotion of lean body mass, and others. The exact mechanisms of nutritional enhancement for pyruvate are unknown, but have been postulated. Stanko and Bunger ("The Mystery of PYA)[in press]) have reported that significantly enhanced metabolic activities have resulted from the dietary supplemental feeding of pyruvate in mammalian species, including human, at daily dosage levels of about 2–8 grams per day (as much as 100 g of pyruvate per day has been used safely).

Pyruvic acid and its salts, esters, and amide derivatives, have many inherent problems when used as nutritional supplements. For example, the calcium salt of pyruvic acid is a hygroscopic material that decomposes rapidly when mixed with water, and it is difficult to make on the industrial scale required for a commercially viable product. The sodium and potassium salts are easier to produce on such a scale, however are less desirable for dietary supplementation due to the rather high levels of the metals that would be ingested in order to realize any of the health benefits of the pyruvate. Also, the taste is not compatible with many drink or confectionery blends pyruvic acid esters and amides have also been prepared, and have been shown to have nutritional enhancement properties. Unfortunately, these pyruvate salts, esters and amides have all been shown to be labile molecules, with lifetimes unacceptable for use as dietary supplements in the commercial marketplace.

SUMMARY OF THE INVENTION

The present invention is a novel composition having a polyol-derived pyruvate (2-keto-propionic-acid) moiety as the chief component. The present invention also includes methods for preparing such compositions.

It is the object of the present invention to provide a composition that is stable for use as a nutritional supplement to the human diet.

It is the prime object of the present invention to provide a stable composition that when administered orally results in a nutritionally beneficial digestive mixture.

BRIEF DESCRIPTION OF THE DRAWING

FIG. 1 is a general structure of the compositions of the present invention.

DETAILED DESCRIPTION OF THE INVENTION

The present invention is a novel, general composition comprising a polyol (glycerol, sugars, carbohydrates, and other 1,2 diols) derived pyruvate, where the 2-keto group of the pyruvate has been transformed to a ketal moiety. The carboxyl group at carbon 1 of the present invention may be present as an ester, acid, or amide, or acid salt. In accordance with the provisional application filed Aug. 5, 1997 (Serial No. 60/054,766), the composition of the present invention may be polymeric, or monomeric.

Derivatives of pyruvic acid described by the present invention, and in accordance with the provisional application filed Aug. 5, 1997 (Serial No. 60/054,766), have been discovered to provide appreciable stability to the pyruvate moiety, and to afford new chemical species that when orally administered to the human system impart health benefits. The general structure of the compositions of the present invention is described in FIG. 1.

The compositions of the present invention may be prepared by the following methods. A first general method (Method A) uses a pyruvate ester (or amide), soluble polyol and acid (and solvent if desired) as the starting materials, and is outlined in Scheme 1.

STEP 1: Formation of pyruvate ketal by direct acid catalyzed ketalization of polyol.

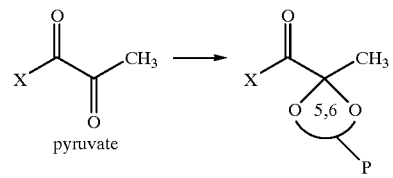

STEP 2: Hydrolysis of pyruvate ester ketal to form acid salt, or acid.

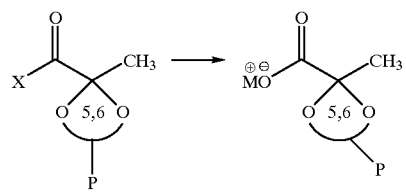

STEP 3: Formation of acid chloride of pyruvate ketal

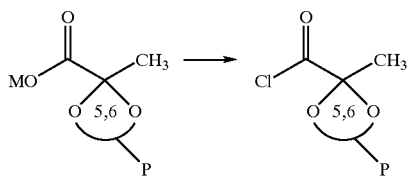

STEP 4: Formation of acid derivative of pyruvate ketal

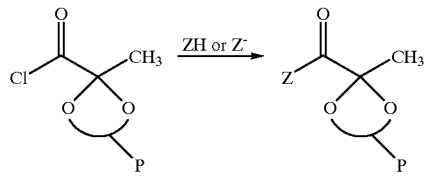

EXAMPLE 1—Method A

General synthetic method for preparation of pyruvate saccharide ketals from pyruvate esters To a stirred solution of ethyl pyruvate (10 g) and glycerin (14.5 g) was added 11 g of boron trifluoride-ether complex (Aldrich), and this was stirred at ambient temperature for about 18 hours. To this was added 25 ml of water with 100 ml of dichloromethane, the layers were then separated, and the dichloromethane layer was washed twice with 20 ml of water, and then the dichloromethane was removed via vacuum distillation to give the reaction product.

EXAMPLE 2—Method B

General synthetic method for preparation of pyruvate saccaride ketals from pyruvic acid Pyruvic acid (10 g) was added, with stirring at ambient temperature, to 30 g of glycerin, and to the resulting homogeneous solution was added 10 drops of concentrated hydrochloric acid. This was warmed to an internal temperature of between 35° C. and 45° C. for about 48 hours, then let cool to room temperature to yield the reaction product as a viscous oil.

EXAMPLE 3

To the reaction product of Example 2 was added 11 g of carnitine to bring the pH of the mixture to about 4–7.

EXAMPLE 4

Preparation of a sodium salt of said invention. (STEP 2, where X=OH, M=Na, and polyol is glycerol).

To the reaction product of Example 1 was added 75 ml of water followed by the dropwise addition of about 10 g of a 40% sodium hydroxide solution (enough sodium hydroxide to give a pH of about 5–7), and the resulting solution was stirred for about 1 hour, then the water was removed via vacuum to yield a white solid reaction product.

EXAMPLE 5

Preparation of a glycerol ester of said invention. (STEP 3, where M=Na, and polyol is glycerol).

To the reaction product of example 4 was added 75 ml of toluene with stirring in an ice bath, followed by 11 g of oxallyl chloride, and to this was added 1 drop of dimethylformamide. The resulting mixture was stirred for about 2 hours to give the corresponding glycerol ketal pyruvic acid chloride. To this was added 12 g of glycerin in 50 ml of ethyl acetate, and 20 g of sodium carbonate, and the resulting mixture was stirred about 18 hours. This was filtered and then washed twice with 25 ml of water, and then the solvent was removed at about 30° C. under vacuum to give the reaction product as a viscous liquor.

EXAMPLE 6

Preparation of a creatine salt of said invention. (STEP 2, where X=OCH$_2$CH$_3$, M=Na, and polyol is glycerol, followed by addition of creatine (H$_2$NC(=NH)N(CH$_3$)CH$_2$CO$_2$H)).

To the reaction product of Example 1 was added 75 ml of water followed by the dropwise addition of about 10 g of a 40% sodium hydroxide solution (enough sodium hydroxide to give a pH of about 5–7), and the resulting solution was stirred for about 1 hour, then the water was removed via vacuum to yield a white solid reaction product. This was dissolved in 50 ml of water, and to this was added 14 g of creatine hydrochloride, and the resulting solution was stirred for about 1 hour. The solvent was removed to give the reaction product.

EXAMPLE 7

Preparation of a glycerin-3-phosphate ester of the present invention. (STEP 4, where Z=glycerol 3 phosphate).

To the reaction product of example 4 was added 75 ml of toluene with stirring in an ice bath, followed by 11 g of oxallyl chloride, and to this was added 1 drop of dimethylformamide. The resulting mixture was stirred for about 2 hours to give the corresponding glycerol ketal pyruvic acid chloride. To this was added 21 g of glycerin-3-phosphate as a suspension in 50 ml of ethyl acetate, and 20 g of sodium carbonate, and the resulting mixture was stirred about 2 hours, then heated to about 45° C. for an additional 18 hours. This was filtered and the solvent was removed at about 3° C. under vacuum to give the reaction product as a solid.

EXAMPLE 8 Preparation of glycerol ketal of pyruvamide

A solution of pyruvamide (10 g) in 150 ml of acetonitrile was added 12 grams of glycerin followed by the addition of 15 g of boron trifluoride ether complex (Aldrich). This was stirred at ambient temperature for about 4 hours, then 75 mL of water was added and the layers were separated. The acetonitrile layer was washed twice with 75 ml of water, and then the acetonitrile was removed via vacuum distillation to give the reaction product as an amorphous solid.

What is claimed is:

1. A polyol ketal of the formula:

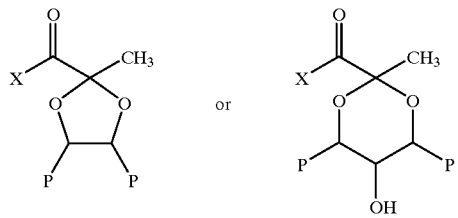

Wherein:

X represents OR NR$_2$, OH, or OM;

R represents hydrogen, an alkyl, or a polyol;

M represents Na, K, Mg, Ca;

P represents hydrogen, polyol, alcohol, —CH(OH)CH(OH)R, CH$_2$OH, but P may not represent hydrogen in the first structure.

* * * * *